United States Patent [19]

Takano

[11] Patent Number: 4,579,962

[45] Date of Patent: Apr. 1, 1986

[54] ENHANCED 2-HYDROXY-4-METHYLTHIOBUTANOIC ACID COMPOSITIONS AND METHOD OF PREPARATION

[75] Inventor: Masaharu Takano, St. Louis, Mo.

[73] Assignee: Monsanto Company, St. Louis, Mo.

[21] Appl. No.: 583,463

[22] Filed: Feb. 24, 1984

[51] Int. Cl.[4] ............ C07F 3/06; C07F 3/02; C07F 1/04

[52] U.S. Cl. ............ 556/131; 514/494; 514/557; 562/581

[58] Field of Search ............ 260/429.9; 562/581; 514/494, 557; 556/131

[56] References Cited

U.S. PATENT DOCUMENTS 3,941,818 3/1976 Abdel-Monem ............ 260/429.9
4,046,793 9/1977 Baccini et al. ............ 260/429.9 X
4,396,552 8/1983 Knoblock et al. ............ 260/429.9 X

OTHER PUBLICATIONS

Chemical Abstracts 94 139243r (1981).

*Primary Examiner*—Helen M. S. Sneed
*Attorney, Agent, or Firm*—Dennis R. Hoerner, Jr.; James W. Williams, Jr.

[57] ABSTRACT

Enhanced HMBA compositions which comprise 2-hydroxy-4-methylthiobutanoic acid and at least one metallic cation selected from the group consisting of sodium, potassium, magnesium and zinc ions are disclosed. The enhanced HMBA compositions are prepared by contacting HMBA and predetermined metallic cation(s) in molar ratios which are hyperstoichiometric and less than about five.

10 Claims, No Drawings

ENHANCED 2-HYDROXY-4-METHYLTHIOBUTANOIC ACID COMPOSITIONS AND METHOD OF PREPARATION

BACKGROUND OF THE INVENTION

The present invention relates to 2-hydroxy-4-methylthiobutanoic acid, an analogue of the essential amino acid methionine, commonly referred to as methionine hydroxy analogue. More particularly, the present invention relates to methionine hydroxy analogue compositions which have a substantially higher 2-hydroxy-4-methylthiobutanoic acid content than compositions reported heretofore.

Various methods for preparing methionine are known. For example, the synthesis of methionine from methyl mercaptan and acrolein involves the preparation of methylmercaptopropionaldehyde which is reacted with hydrocyanic acid to form 2-hydroxy-4-methylthiobutyronitrile which is subsequently aminated and hydrolyzed to methionine. Unfortunately, the reaction of 2-hydroxy-4-methylthiobutyronitrile with ammonia is a difficult and costly procedure requiring the use of high pressure apparatus. It was subsequently found that methionine analogues such as 2-hydroxy-4-methylthiobutanoic acid, hereinafter referred to as HMBA, are virtually as effective as methionine for nutritional uses, particularly as a poultry feed supplement. However, the crystalline form of HMBA has a melting point between 38° C. and 42° C. depending on the purity, rendering it susceptible to liquid-solid phase change upon storage or use at ambient temperatures.

The salts of HMBA have higher melting points than the free acid form of HMBA. The sodium, potassium, magnesium and zinc salts of HMBA have previously been disclosed since these cations are minerals which must be supplemented in animal feeds. Compositions and methods disclosed for preparing salts of HMBA with the above-identified cations teach reacting essentially stoichiometric amounts of HMBA and the hydroxide, oxide, bicarbonate, carbonate or acetate of the selected cation in aqueous solution, for example see Belg. Pat. No. 882,067 and U.K. Pat. Appl. No. G.B. 2,044,775A. However, these salts are, in general, highly hygroscopic and show poor storage stability before and after mixing with animal feeds.

It is therefore the overall object of the present invention to provide enhanced HMBA compositions having substantially higher HMBA equivalent per unit weight than the ionic salts disclosed heretofore.

It is an object of the present invention to provide enhanced HMBA compositions which are less hygroscopic than the ionic salts disclosed heretofore.

It is yet another object of the present invention to provide a method for preparing the enhanced HMBA compositions embraced by the present invention.

These and other objects, features, and advantages of the present invention will become evident to those skilled in the art from the following description.

SUMMARY OF THE PRESENT INVENTION

The present invention provides enhanced compositions of 2-hydroxy-4-methylthiobutanoic acid with sodium, potassium, magnesium and zinc having substantially greater molar ratios of HMBA equivalency to predetermined metallic cation(s) than the ionic salts disclosed heretofore. The enhanced HMBA compositions are advantageous since these compositions have higher methionine activity per unit weight and are, in general, less hygroscopic than ionic salts consisting of stoichiometric amounts of HMBA and the metallic cation. The enhanced HMBA compositions of the present invention can be easily prepared by contacting hyperstoichiometric amounts of 2-hydroxy-4-methylthiobutanoic acid with suitable sodium, potassium, magnesium and zinc compounds in solution, slurry, or powder form.

DETAILED DESCRIPTION OF THE INVENTION

The present invention embraces in its broadest aspect the surprising discovery that enhanced HMBA compositions can be prepared from 2-hydroxy-4-methylthiobutanoic acid and suitable sodium, potassium, magnesium or zinc compounds in which HMBA is present in hyperstoichiometric amounts and less than about five moles of HMBA equivalency per mole of the above-identified metallic cations. By "hyperstoichiometric" is meant that HMBA and the metallic cation are present in a molar ratio greater than that corresponding to ionic salt formation. For example, enhanced HMBA compositions of the present invention comprising magnesium and HMBA have a molar ratio of HMBA equivalency to magnesium ion greater than two and less than about five.

The usual commercial form of HMBA is the optically racemic D,L-HMBA mixture. It should be understood that while the HMBA compositions referred to hereinafter are racemic mixtures, the individual D- and L-isomers of HMBA can be converted to the enhanced HMBA compositions of the present invention by the procedures described hereinafter. Hence, for purposes of the present invention by "HMBA" is meant either the D- or L-isomer of 2-hydroxy-4-methylthiobutanoic acid or any mixture of the two above-described isomers thereof. It should be further understood that by "HMBA equivalent" is meant the amount of free HMBA which corresponds to the HMBA present in the composition whether in free acid or ionized form. For example, while not fully understood, a composition comprising three moles of HMBA equivalent per mole of sodium is believed to exist as a complex which comprises two moles of free acid and one mole of ionized HMBA per mole of sodium ion.

The above-identified metallic cations can be supplied to the present invention in numerous forms. Suitable compounds include the hydroxides, oxides, bicarbonates, carbonates, acetates, halides, nitrates, phosphates and sulfates. The oxides, hydroxides, bicarbonates and carbonates are preferred since their reaction rates are faster and their conversions are usually more complete. Moreover, by-products such as acetic acid (acetates), hydrochloric acid (chlorides), nitric acid (nitrates), phosphoric acid (phosphates), and sulfuric acid (sulfates) have to be removed by washing repeatedly with water. As a result, the yield is reduced since some of the enhanced composition is lost in the washing process.

The reaction rate of HMBA with a particular metallic cation is generally affected by the particle size, and solubility of the cation donor in water and liquid HMBA. While reaction will proceed in a nearly anhydrous system, the presence of water is preferred at a concentration between about 2 and 50 wt.% to accelerate the reaction rate and to aid in producing homogeneous products. The presence of water is particularly advantageous when using the oxides, carbonates, or bicarbonate compounds of the predetermined metallic cation.

The present invention embraces a method for producing the above-described compositions in which HMBA is contacted with a metallic cation selected from the group consisting of sodium, potassium, magnesium and zinc ions in molar ratios which are hyperstoichiometric and less than about five. While drying the enhanced compositions prepared as described-above is not considered necessary in all instances, drying is preferred in cases where liquid by-products such as water are produced. Although it is anticipated that in most instances the enhanced HMBA compositions produced would comprise HMBA and a single predetermined metallic cation, one may also produce enhanced compositions comprising a plurality of metallic cations.

The sodium salt of HMBA prepared by contacting one mole of HMBA with one mole of aqueous sodium hydroxide has a melting point of about 152° C., but is highly hygroscopic. Enhanced HMBA compositions comprising more than one and less than about five moles of HMBA equivalency per mole of sodium ion show high HMBA equivalency and reduced hygroscopicity. Enhanced HMBA compositions comprising about two moles of HMBA equivalency per mole of sodium ion can be easily crystallized from aqueous solution by evaporation of water. Contacting liquid HMBA with sodium bicarbonate or sodium carbonate makes the drying process much easier since the carbon dioxide by-product evaporates off without external heating. When the molar ratio of HMBA equivalent to sodium ion is increased beyond three the composition becomes a dough-like material. However, the hygroscopicity is still much lower than the conventional ionic salt, see examples 1 through 4.

The conventional potassium salt of HMBA prepared by contacting one mole of HMBA with one mole of aqueous potassium hydroxide is highly hygroscopic and a grease-like material at 25° C. Enhanced HMBA compositions comprising about two moles of HMBA equivalency per mole of potassium ion can be easily crystallized from aqueous solution by evaporation of water. Alternately, contacting liquid HMBA with potassium carbonate or potassium bicarbonate makes the drying process much easier as described above for enhanced HMBA/sodium compositions.

An enhanced HMBA composition comprising greater than two moles and less than about five moles of HMBA per mole of magnesium ion can be easily prepared by contacting aqueous HMBA and magnesium hydroxide in the appropriate molar ratio. When three moles of HMBA are contacted with one mole of magnesium hydroxide a powdery reaction product is obtained. As the molar ratio of HMBA to magnesium ion increases, the reaction product becomes gummy and the hygroscopicity increases slightly. The reaction products become slightly wet at about 130° C. and decompose at a temperature greater than 280° C.

Zinc and HMBA also form enhanced compositions having greater than two and less than about five moles of HMBA equivalency per mole of zinc ion. These compositions are preferably obtained using zinc oxide as the cation donor. When the molar ratio of HMBA to zinc ion is between two and three and one-half the reaction product is powdery. When the molar ratio exceeds three and one-half the reaction product becomes gummy. While the hygroscopicity remains fairly stable at molar ratios of HMBA equivalency to zinc ion below four, the hygroscopicity increases appreciably when the molar ratio of HMBA and zinc ion is four and higher. The enhanced HMBA compositions become slightly wet at about 134° C. and totally melt at about 247° C. after slight discoloration.

In the following examples, the HMBA equivalencies in HMBA liquids, salts and enhanced HMBA compositions were determined by titration with a standard bromide/bromate solution. The hygroscopicity of the materials is determined by the increase in weight after exposure to a 100% relative humidity atmosphere at 25° C. for one week. These examples are included for illustrative purposes only and are not intended, in any way, to limit the scope of the present invention.

EXAMPLE 1

16.9 g of an aqueous 89% by weight HMBA solution, 10 g of water and various amounts of sodium hydroxide pellets were mixed in an evaporating dish with a spatula at 25° C., and water was evaporated off at 70° C. overnight. The resulting reaction mixtures showed the following compositions and material characteristics:

| Molar Ratio of HMBA/Na | HMBA Equiv. | | Wt. Inc. in a Week (wt. %) | Melting Point (°C.) |
| --- | --- | --- | --- | --- |
| | Calc'd. (wt %) | Meas'd. (wt %) | | |
| 1.0 | 86.7 | 88.3 | 70.5 | 152 |
| 1.5 | 90.7 | 91.0 | 48.3 | 101 |
| 1.75 | 91.9 | 92.9 | 31.7 | 106 |
| 2.0 | 92.9 | 94.8 | 18.2 | 113 |

When two moles of HMBA were contacted with one mole of sodium hydroxide, the resulting reaction product was less hygroscopic than the conventional salt comprising one mole of HMBA equivalency and one mole of sodium ion.

EXAMPLE 2

16.9 g of an aqueous 89% by weight HMBA solution and various amounts of sodium bicarbonate powder were mixed in an evaporating dish with a spatula at 25° C. Carbon dioxide gas was vigorously generated. The resulting reaction mixtures dried at 70° C. overnight showed the following compositions and material characteristics:

| Molar Ratio of HMBA/Na | HMBA Equiv | | Wt. Inc. in a Week (wt. %) | Melting Point (°C.) |
| --- | --- | --- | --- | --- |
| | Calc'd. (wt. %) | Meas'd. (wt. %) | | |
| 1.0 | 86.7 | 83.0 | 59.9 | 110 |
| 1.5 | 90.7 | 91.0 | 44.7 | 97 |
| 1.75 | 91.9 | 93.6 | 35.3 | 104 |
| 2.0 | 92.9 | 95.5 | 16.3 | 106 |

A less hygroscopic reaction product was obtained when two moles of HMBA had been contacted with one mole of sodium bicarbonate.

EXAMPLE 3

16.9 g of an aqueous 89% by weight HMBA solution and various amounts of sodium bicarbonate powder were contacted in the same way as done in Example 2. However, the resulting reaction mixtures were dried overnight in a vacuum oven at 40° C. with 188 mm Hg nitrogen gas purge. The resulting reaction mixtures showed the following compositions and material characteristics.

| Molar Ratio of HMBA/Na | HMBA Equiv. Calc'd. (wt %) | HMBA Equiv. Meas'd. (wt %) | Wt. Inc. in a Week (wt %) | Melting Point (°C.) |
| --- | --- | --- | --- | --- |
| 2.5 | 94.2 | 93.6 | 9.9 | 100 |
| 3.0 | 95.1 | 95.4 | 11.6 | 76 |
| 4.0 | 96.3 | 96.8 | 15.3 | 56 |
| 5.0 | 97.0 | 97.3 | 11.1 | 35 |

Powdery reaction products were obtained when the molar ratio of HMBA equivalency to sodium ion was between two and three. When the molar ratio was greater than or equal to four, the compositions became dough-like materials.

EXAMPLE 4

16.9 g of an aqueous 89% by weight HMBA solution and various amounts of sodium carbonate powder were mixed in an evaporating dish with a spatula at 25° C. The reaction products were dried at 70° C. overnight. The resulting compositions and material characteristics were as follows:

| Molar Ratio of HMBA/Na | HMBA Equiv. Calc'd. (wt %) | HMBA Equiv. Meas'd. (wt %) | Wt. Inc. in a Week (wt %) | Melting Point (°C.) |
| --- | --- | --- | --- | --- |
| 1.0 | 86.7 | 84.1 | 43.0 | 101 |
| 1.5 | 90.7 | 90.2 | 38.1 | 94 |
| 1.75 | 91.9 | 91.9 | 19.8 | 99 |
| 2.0 | 92.9 | 93.6 | 21.7 | 100 |

The reaction rate was slower than that for sodium bicarbonate as described in Example 3. Less hygroscopic powdery reaction products were obtained when the molar ratio of HMBA equivalency to sodium ion was about two.

EXAMPLE 5

16.9 g of an aqueous 89% by weight HMBA solution, 10 g of water and various amounts of potassium hydroxide pellets were mixed and dried in the same way as described in Example 1. The resulting reaction products showed the following compositions and material characteristics:

| Molar Ratio of HMBA/K | HMBA Equiv. Calc'd. (wt %) | HMBA Equiv. Meas'd. (wt %) | Wt. Inc. in a Week (wt %) | Melting Point (°C.) |
| --- | --- | --- | --- | --- |
| 1.0 | 79.2 | 78.6 | 50.7 | <25 |
| 2.0 | 88.5 | 86.6 | 38.1 | 58 |

The conventional potassium salt is highly hygroscopic. However, when two moles of HMBA and one mole of potassium hydroxide were reacted, the hygroscopicity of reaction product could be reduced.

EXAMPLE 6

16.9 g of an aqueous 89% by weight HMBA solution and various amounts of potassium carbonate powder were mixed in an evaporating dish in the same way as described in Example 1. The reaction mixtures were dried overnight in a vacuum oven at 40° C. under a 188 mm Hg nitrogen gas purge. The resulting reaction products showed the following compositions and material characteristics:

| Molar Ratio of HMBA/K | HMBA Equiv. Cal'd. (wt %) | HMBA Equiv. Meas'd. (wt %) | Wt. Inc. in a Week (wt %) | Melting Point (°C.) |
| --- | --- | --- | --- | --- |
| 1.0 | 79.2 | 73.1 | 42.1 | 59 |
| 2.0 | 88.5 | 86.8 | 24.5 | 64 |
| 3.0 | 92.0 | 86.8 | 7.9 | 29 |
| 4.0 | 93.9 | 89.2 | 5.9 | <25 |
| 5.0 | 95.1 | 90.2 | 5.0 | <25 |

Although free flowing powdery products were not obtained, the hygroscopicity of the enhanced HMBA compositions significantly decreased when more than two moles of HMBA had been contacted with a half mole of potassium carbonate.

EXAMPLE 7

16.9 g of an aqueous 89% by weight HMBA solution and various amounts of magnesium hydroxide were mixed and dried in the same ways as described in Example 1. The resulting reaction mixtures showed the following composition and material characteristics:

| Molar Ratio of HMBA Mg | HMBA Equiv. Cal'd. (wt %) | HMBA Equiv. Meas'd. (wt %) | Wt. Inc. in a Week (wt %) | Melting Point (°C.) |
| --- | --- | --- | --- | --- |
| 2.0 | 92.5 | 94.0 | 12.3 | >280 |
| 2.5 | 93.9 | 94.0 | 13.5 | >280 |
| 3.0 | 94.9 | 95.2 | 14.9 | >280 |
| 3.5 | 95.6 | 95.7 | 16.8 | >280 |
| 4.0 | 96.1 | 95.9 | 21.1 | >280 |
| 5.0 | 96.9 | 96.7 | 17.6 | >280 |

When the molar ratio of HMBA equivalency to magnesium ion was greater than two, the reaction products became slightly wet at about 130° C. and started discoloring at about 170° C. before decomposing at a temperature greater than 280° C. Reaction products were relatively free-flowing powder when the molar ratio of HMBA equivalency to magnesium ion was less than about three.

EXAMPLE 8

16.9 g of an aqueous 89% by weight HMBA solution and various amounts of zinc oxide were mixed and dried in the same ways as described in Example 1. The resulting reaction mixtures showed the following compositions and material characteristics:

| Molar Ratio of HMBA/Zn | HMBA Equiv. Cal'd. (wt %) | HMBA Equiv. Meas'd (wt %) | Wt. Inc. in a Week (wt %) | Melting Point (°C.) |
| --- | --- | --- | --- | --- |
| 2.0 | 82.0 | 78.5 | 2.8 | 255 |
| 2.5 | 85.1 | 85.7 | 5.8 | 247 |
| 3.0 | 87.9 | 88.9 | 5.7 | 248 |
| 3.5 | 88.9 | 89.7 | 8.4 | 244 |
| 4.0 | 90.2 | 90.4 | 17.2 | 246 |
| 5.0 | 92.0 | 90.9 | 12.6 | 244 |

When the molar ratio of HMBA equivalency to zinc ion was greater than two, the reaction products became slightly wet at about 134° C. before totally melting at about 246° C. Reaction products were powdery and relatively free-flowing when the molar ratio of HMBA equivalency to zinc ion was less than three.

EXAMPLE 9

15.0 g of a 98% by weight HMBA solution having 1.6% by weight water was mixed with sodium bicarbonate, potassium carbonate, magnesium hydroxide and zinc oxide to form enhanced compositions of the appropriate metal and dried in the same way as described in Example 1. Reaction proceeded, but slowly. The resulting reaction products showed the following compositions and material characteristics:

| Molar Ratio of HMBA/Metal | HMBA Equiv. Calc'd. (wt %) | HMBA Equiv. Mead'd. (wt %) | Wt. Inc. in a Week (wt %) | Melting Point (°C.) |
| --- | --- | --- | --- | --- |
| 2/Na | 92.9 | 89.1 | 20.9 | 103 |
| 2/K | 88.5 | 86.5 | 24.1 | <25 |
| 3/Mg | 94.9 | 95.4 | 17.5 | >280 |
| 3/Zn | 87.9 | 88.8 | 5.0 | 247 |

HMBA highly polymerized when the enhanced composition prepared using potassium carbonate was dried at 70° C.

I claim:

1. A composition consisting essentially of 2-hydroxy-4-methylthiobutanoic acid and at least one metallic cation selected from the group consisting of sodium, potassium, magnesium and zinc ions in which the molar ratio of 2-hydroxy-4-methylthiobutanoic equivalency to metallic cation is hyperstoichiometric and less than about five.

2. A composition consisting essentially of 2-hydroxy-4-methylthiobutanoic acid and sodium ion in which the molar ratio of 2-hydroxy-4-methylthiobutanoic acid equivalency to sodium ion is greater than one and less than about five.

3. A composition consisting essentially of 2 hydroxy-4-methylthiobutanoic acid and potassium ion in which the molar ratio of 2-hydroxy-4-methylthiobutanoic acid equivalency to potassium ion is greater than one and less that about five.

4. A composition consisting essentially of 2-hydroxy-4-methylthiobutanoic acid and magnesium ion in which the molar ratio of 2-hydroxy-4-methylthiobutanoic acid equivalency to magnesium ion is greater than two and less than about five.

5. A composition consisting essentially of 2-hydroxy-4-methylthiobutanoic acid and zinc ion in which the molar ratio of 2-hydroxy-4-methylthiobutanoic acid equivalency to zinc ion is greater than two and less than about five.

6. A method for preparing enhanced 2-hydroxy-4-methylthiobutanoic acid compositions which comprises contacting 2-hydroxy-4-methylthiobutanoic acid and at least one metallic cation selected from the group consisting of sodium, potassium, magnesium and zinc ions from a suitable cation donor wherein, the molar ratio of 2-hydroxy-4-methylthiobutanoic acid to metallic cation is hyperstoichiometric and less than about five.

7. The method of claim 6 further comprising drying the enhanced 2-hydroxy-4-methylthiobutanoic acid compositions.

8. The method of claim 6 in which the metallic cation donor is selected from the group consisting of hydroxides, oxides, bicarbonates, carbonates, acetates, halides, nitrates, phosphates, and sulfates.

9. The method of claim 6 in which the metallic cation donor is selected from the group consisting of hydroxides, oxides, bicarbonates and carbonates.

10. The method of claim 6 further comprising the presence of water.

* * * * *

UNITED STATES PATENT AND TRADEMARK OFFICE
CERTIFICATE OF CORRECTION

PATENT NO.  : 4,579,962
DATED       : April 1, 1986
INVENTOR(S) : Masaharu Takano It is certified that error appears in the above—identified patent and that said Letters Patent is hereby corrected as shown below:

Column, 2, line 9, "and" should be -- or --.

Column 4, line 9, "liquids" should be -- liquid --.

Column 6, EXAMPLE 7, second line of caption on
         the first column should be -- of HMBA/Mg --.

Column 8, Claim 3, line 5, "that" should be -- than --.

Signed and Sealed this

Twenty-second Day of July 1986

[SEAL]

Attest:

DONALD J. QUIGG

Attesting Officer

Commissioner of Patents and Trademarks